United States Patent
Albert et al.

(10) Patent No.: US 9,079,926 B2
(45) Date of Patent: *Jul. 14, 2015

(54) METHOD FOR TREATING RESIDUES CONTAINING SALT, PRODUCED DURING THE PRODUCTION OF AMINO-FUNCTIONAL ORGANOSILANES

(75) Inventors: Philipp Albert, Lörrach (DE); Eckhard Just, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 444 days.

This patent is subject to a terminal disclaimer.

(21) Appl. No.: 12/995,871

(22) PCT Filed: Apr. 20, 2009

(86) PCT No.: PCT/EP2009/054649
§ 371 (c)(1),
(2), (4) Date: Feb. 4, 2011

(87) PCT Pub. No.: WO2009/146972
PCT Pub. Date: Dec. 10, 2009

(65) Prior Publication Data
US 2011/0146535 A1    Jun. 23, 2011

(30) Foreign Application Priority Data
Jun. 3, 2008 (DE) .......................... 10 2008 002 183

(51) Int. Cl.
*C07F 7/10* (2006.01)
*C07F 7/18* (2006.01)

(52) U.S. Cl.
CPC .................................... *C07F 7/1892* (2013.01)

(58) Field of Classification Search
USPC ......................... 556/478, 423, 413
See application file for complete search history.

(56) References Cited

U.S. PATENT DOCUMENTS

| | | | |
|---|---|---|---|
| 4,526,996 A | | 7/1985 | Kilgour et al. |
| 5,260,470 A | | 11/1993 | Goebel et al. |
| 5,616,755 A | | 4/1997 | Seiler et al. |
| 5,698,726 A | | 12/1997 | Rauleder et al. |
| 5,760,019 A | * | 6/1998 | Sieburth et al. ............. 514/63 |
| 5,808,123 A | * | 9/1998 | Balduf et al. ............... 556/413 |
| 6,150,551 A | | 11/2000 | Kropfgans et al. |
| 6,177,584 B1 | | 1/2001 | Loewenberg et al. |
| 6,423,858 B1 | | 7/2002 | Schwarz et al. |
| 6,500,883 B1 | | 12/2002 | Mack et al. |
| 6,696,587 B2 | | 2/2004 | Jenkner |
| 6,750,361 B2 | | 6/2004 | Kropfgans et al. |
| 6,963,006 B2 | * | 11/2005 | Tsui et al. ................ 556/410 |

FOREIGN PATENT DOCUMENTS

| | | |
|---|---|---|
| DE | 41 30 643 | 3/1993 |
| DE | 101 40 563 | 2/2003 |
| EP | 1 111 002 | 6/2001 |

OTHER PUBLICATIONS

International Search Report issued Aug. 4, 2009 in PCT/EP09/054649 filed Apr. 20, 2009.
U.S. Appl. No. 12/988,637, filed Oct. 20, 2010, Albert, et al.
U.S. Appl. No. 12/995,852, filed Dec. 2, 2010, Just, et al.
U.S. Appl. No. 10/246,525, filed Sep. 19, 2002, Kahsnitz, et al.
U.S. Appl. No. 13/062,225, filed Mar. 4, 2011, Weissenbach, et al.
Nonpolar Molecules at http://www.shs.d211.org/science/faculty/S2B/Old%20Stuff/nonpolar_molecu . . . Accessed Jul. 9, 2014 (2 pages).
Heptane at http://en.wikipedia.org/wiki/Heptane accessed Jul. 9, 2014 (2 pages).
All about Solvents: Non-polar, Polar Aprotic, and Polar Protic Solvents . . . at http://www.masterorganicchemistry.com/2012/04/27/polar-protic-polar-aprot . . . Accessed Jul. 9, 2014 (4 pages).

* cited by examiner

*Primary Examiner* — Sudhakar Katakam
*Assistant Examiner* — Pancham Bakshi
(74) *Attorney, Agent, or Firm* — Oblon, McClelland, Maier & Neustadt, L.L.P.

(57) ABSTRACT

The invention relates to a method for treating an ammonium halogenide and/or residue containing organic aminhydrohalogenides, produced during the production of an amino-functional organosilane of general formula (I) $R_2N[(CH_2)_2NH]_z(Z)Si(R'')_n(OR')_{3-n}$ (Ia), wherein the production of the amino-functional organosilane according to formula (Ia) is based on the conversion of a halogen-functional organosilane of general formula (II) $X-Z-Si(R'')_n(OR')_{3-n}$ (II), with excess ammonia or an organic amine of general formula (III) $RNH[(CH_2)_2NH]_zR$ (III) and subsequently separating and treating the raw product and the resulting residue containing salt. The treatment consists of adding an essentially non-polar organic solvent and an aqueous lye to the residue. The mixture is reacted, subsequently the aqueous phase is separated from the organic phase, the organic solvent contained in the organic phase is removed from said phase and the residual organic phase is recovered.

17 Claims, No Drawings

METHOD FOR TREATING RESIDUES CONTAINING SALT, PRODUCED DURING THE PRODUCTION OF AMINO-FUNCTIONAL ORGANOSILANES

The present invention relates to a novel process for working up salt-containing residues as obtained in the preparation of an amino-functional organosilane by reacting a halogen-functional organosilane with excess ammonia or an organic amine. The invention further relates to compositions containing specific bis- and tris-amino-functional organosilanes, and to the use thereof. Amino-functional organosilanes are also referred to hereinafter as aminosilanes for short. In addition, a residue containing ammonium halide and/or organic amine hydrohalides as obtained in the preparation of amino-functional organosilanes by reacting a halogen-functional organosilane with ammonia or an organic amine is also referred to here and hereinafter as salt-containing residue for short, or as residue in an even shorter form.

Aminosilanes have a wide spectrum of application. They are used, for example, for glass fiber sizes or in the foundry industry as processing aids; they likewise serve as adhesion promoters for storage-stable resins.

It has long been known that amino-functional organosilanes can be prepared especially from chlorine-functional organosilanes and ammonia or organic amines; in this case, the ammonium chloride formed or the organic amine hydrochloride formed have to be removed (DE-C 10 23 462, DE-C 27 49 316, DE-C 27 53 124, EP 0 702 017 A2, EP 0 741 137 A2, EP 0 849 271 A2, EP 1 295 889 A2).

The procedure in EP 1 262 484 A2, EP 1 209 162 A2 and DE 101 40 563 A1 is to conduct the preparation process over various pressure stages, as a result of which, inter alia, the consequences from the problems of salt caking were reduced.

A common feature of the processes for preparing amino-functional organosilanes by reacting corresponding organo-halo-functional silanes with ammonia or an amine is that salt-containing residues are obtained, which generally have to be disposed of. Said residues may, for example, contain ammonium chloride, 3-aminopropyltriethoxysilane hydrochloride (known as AMEO hydrochloride), and also bis-AMEO hydrochloride or tris-AMEO hydrochloride, and possibly corresponding hydrolysis-related disiloxanes, etc. The search for a utilization of such residues generally fails because of the high chloride content of the residues.

It was therefore an object of the present invention to find a further means of added-value workup in the preparation of amino-functional organosilanes. A particular wish was to supply salt-containing residues from the preparation of amino-functional organosilanes to an economic use.

The stated object is achieved in accordance with the invention according to the details in the claims.

It has been found that, surprisingly, hydrochlorides formed from aminosilanes can be worked up with a strongly alkaline aqueous solution without hydrolyzing aminoalkoxysilane present in a significant amount. The present process is generally applicable advantageously to all amino-functional organosilanes. More particularly, this advantageously provided a simple and economic means of added-value workup of a residue from an aminosilane synthesis, especially of a residue from the distillation of an aminosilane synthesis.

It has thus been found, surprisingly, that a residue containing ammonium halides and/or organic amine hydrohalides in particular, from the preparation of an amino-functional organosilane, the preparation being based on the reaction of a halogen-functional, preferably chlorine-functional, organoalkoxysilane with excess ammonia or an organic amine, preferably under pressure and in the liquid phase, and subsequent separation and workup of crude product and salt obtained, can be worked up in a simple and economic manner by optionally first adding an essentially nonpolar organic solvent to said residue, and additionally adding a strong aqueous alkali, allowing them to react—preferably while controlling the duration of the reaction—, then, after the formation of the two phases, separating the aqueous phase from the organic phase, and removing the organic solvent from the organic phase to obtain the organic phase remaining in the bottoms. Thus, in a simple and economically viable manner, advantageously after filtration of the organic phase, a clear, generally yellow to deep orange, composition containing high-value bis- and tris-amino-functional organosilanes is obtained, which can be used advantageously with high addition of value for many applications in place of unbridged amino-functional organosilanes. Furthermore, such a composition obtained by the process according to the invention advantageously has a hydrolyzable chloride content of less than 100 ppm by weight down to the detection limit of 6 ppm by weight. Examples of hydrolyzable chloride include organic amine hydrochlorides, ammonium chlorides, chlorosilanes, etc. Hydrolyzable chloride can be determined, for example, potentiographically with silver nitrate.

Bis- or tris-amino-functional organosilanes (also referred to hereinafter as bis- and tris-silylated amines), which are obtained as by-products in the above-mentioned preparation of amino-functional organosilanes, are generally understood to mean bridged aminosilanes. For said amino-functional organosilanes, the general formulae which follow are given by way of example.

Unbridged amino-functional organosilanes, i.e. monosilylated amines, can be represented by the general formula (Ia):

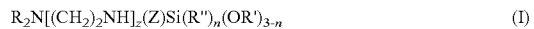

in which R groups are the same or different and R is hydrogen (H) or a linear or branched alkyl group having 1 to 4 carbon atoms, preferably H or n-butyl, R' groups are the same or different and R' is hydrogen (H) or a linear or branched alkyl group having 1 to 8 carbon atoms or an aryl group, preferably methyl or ethyl, R" groups are the same or different and R" is a linear or branched alkyl group having 1 to 8 carbon atoms, such as methyl, ethyl, propyl, butyl, preferably methyl, or an aryl group, Z is a bivalent alkyl group from the group of —CH$_2$—, —(CH$_2$)$_2$—, —(CH$_2$)$_3$—, —(CH$_2$)$_4$— or —(CH$_2$)(CH)CH$_3$(CH$_2$)—, preferably propyl, n is 0, 1, 2 or 3, preferably 0, and z is 0, 1 or 2.

Bis-amino-functional organosilanes, i.e. bis-silylated amines, can be illustrated by the general formula Ib:

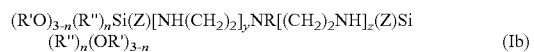

in which R is a hydrogen (H) or a linear or branched alkyl group having 1 to 4 carbon atoms, preferably H or n-butyl, R' groups are the same or different and R' is hydrogen (H) or a linear or branched alkyl group having 1 to 8 carbon atoms or an aryl group, preferably methyl or ethyl, R" groups are the same or different and R" is a linear or branched alkyl group having 1 to 8 carbon atoms, such as methyl, ethyl, propyl, butyl, preferably methyl, or an aryl group, Z groups are the same or different and Z is a bivalent alkyl group from the group of —CH$_2$—, —(CH$_2$)$_2$—, —(CH$_2$)$_3$—, —(CH$_2$)$_4$— or —(CH$_2$)(CH)CH$_3$(CH$_2$)—, preferably propyl, n is independently 0, 1, 2 or 3, preferably 0, and y and z are each independently 0, 1 or 2, preferably $$(H_3CO)_3Si(CH_2)_3NH(CH_2)_3Si(OCH_3)_3 \quad \text{(bis-AMMO)},$$

$$(H_5C_2O)_3Si(CH_2)_3NH(CH_2)_3Si(OC_2H_5)_3 \quad \text{(bis-AMEO)}.$$

Tris-amino-functional organosilanes, i.e. tris-silylated amines, are generally reflected by the general formula (Ic):

$$[(R'O)_{3-n}(R'')_nSi(Z)[NH(CH_2)_2]_x]_3N \quad \text{(Ic)}$$

in which R' groups are the same or different and R' is a hydrogen (H) or a linear or branched alkyl group having 1 to 8 carbon atoms or an aryl group, preferably methyl or ethyl, R'' groups are the same or different and R'' is a linear or branched alkyl group having 1 to 4 carbon atoms, such as methyl, ethyl, propyl, butyl, preferably methyl, or an aryl group, Z groups are the same or different and Z is a bivalent alkyl group from the group of —CH$_2$—, —(CH$_2$)$_2$—, —(CH$_2$)$_3$—, —(CH$_2$)$_4$— or —(CH$_2$)(CH)CH$_3$(CH$_2$)—, preferably propyl, n is independently 0, 1, 2 or 3, preferably 0, and X is independently 0, 1 or 2, preferably $$[(H_3CO)_3Si(CH_2)_3]_3N \quad \text{(tris-AMMO)},$$

$$[(H_5C_2O)_3Si(CH_2)_3]_3N \quad \text{(tris-AMEO)}.$$

The invention thus provides a process for working up a residue containing ammonium halides and/or organic amine hydrohalides from the preparation of an amino-functional organosilane of the general formula (Ia)

$$R_2N[(CH_2)_2NH]_z(Z)Si(R'')_n(OR)_{3-n} \quad \text{(Ia)}$$

in which R groups are the same or different and R is hydrogen (H) or a linear or branched alkyl group having 1 to 4 carbon atoms, R' groups are the same or different and R' is hydrogen (H) or a linear or branched alkyl group having 1 to 8 carbon atoms or an aryl group, R'' groups are the same or different and R'' is a linear or branched alkyl group having 1 to 8 carbon atoms or an aryl group, Z is a bivalent alkyl group from the group of —CH$_2$—, —(CH$_2$)$_2$—, —(CH$_2$)$_3$—, —(CH$_2$)$_4$— or —(CH$_2$)(CH)CH$_3$(CH$_2$)—, n is 0, 1, 2 or 3 and z is 0, 1 or 2, wherein the preparation of the amino-functional organosilane of the formula (Ia) is based on the reaction of a halogen-functional organosilane of the general formula (II)

$$X—Z—Si(R'')_n(OR)_{3-n} \quad \text{(II)}$$

in which X is Cl, Br or I, preferably Cl, Z is a bivalent alkyl group from the group of —CH$_2$—, —(CH$_2$)$_2$—, —(CH$_2$)$_3$—, —(CH$_2$)$_4$— or —(CH$_2$)(CH)CH$_3$(CH$_2$)—, preferably propyl, R' groups are the same or different and R' is a hydrogen (H) or a linear or branched alkyl group having 1 to 8 carbon atoms or an aryl group, preferably methyl or ethyl, R'' groups are the same or different and R'' is a linear or branched alkyl group having 1 to 8 carbon atoms, such as methyl, ethyl, propyl, butyl, preferably methyl, or an aryl group, and n is 0, 1, 2 or 3, preferably 0, with excess ammonia or an organic amine of the general formula (III)

$$RNH[(CH_2)_2NH]_zR \quad \text{(III)}$$

in which R groups are the same or different and R is hydrogen (H) or a linear or branched alkyl group having 1 to 4 carbon atoms, preferably H or n-butyl, and z is 0, 1 or 2, and subsequent separation and workup of crude product and salt obtained to obtain a residue containing ammonium halides and/or organic amine hydrohalides, preferably a residue from the distillative workup of the crude product, by adding an essentially nonpolar organic solvent and an aqueous alkali to said residue, allowing them to react, preferably for a defined period of time, then separating the aqueous phase from the organic phase, and removing the organic solvent from the organic phase to obtain the remaining organic phase.

The halogen-functional organoalkoxysilane of the general formula (II) used is preferably, but not exclusively, 3-chloropropyltrimethoxysilane, 3-chloro-propyltriethoxysilane, 3-chloropropylmethyldimethoxysilane or 3-chloropropylmethyldiethoxysilane. However, it is also possible to use other chloroalkylalkoxysilanes, for example 3-chloropropyldiethylmethoxysilane or 3-chloropropylmethylpropylethoxysilane.

In addition, in the preparation of organoaminoalkyl-functional alkoxysilanes of the general formula (Ia), instead of the ammonia already mentioned, it is advantageously possible to use an organic amine of the general formula (III), for example but not exclusively methylamine, dimethylamine, ethylamine, diethylamine or propylamine.

In said preparation processes for amino-functional organosilanes, residues form, i.e. hydrohalides or halogen salts. The procedure can be illustrated by way of example by the following equations:

$$Cl(CH_2)_3Si(OMe)_3 + 2NH_3 = H_2N(CH_2)_3Si(OMe)_3 + [NR_4]^+Cl^-$$

$$3Cl(CH_2)_3Si(OMe)_3 + 4NH_3 = H_2N(CH_2)_3Si(OMe)_3 + [H_2N[(CH_2)_3Si(OMe)_3]_2]^+Cl^- + 2[NH_4]^+Cl^-$$

$$4Cl(CH_2)_3Si(OMe)_3 + 5NH_3 = H_2N(CH_2)_3Si(OMe)_3 + [HN[(CH_2)_3Si(OMe)_3]_3]^+Cl^- + 3[NH_4]^+Cl^-$$

The residue from the salt removal of the aminosilane preparation process may be present in solid or liquid form and is preferably obtained in a crystallization unit or in a distillative workup of the crude product.

The residue to be worked up in accordance with the invention can optionally first be admixed with an essentially nonpolar organic solvent, preferably selected from the group of hexane, heptane, octane, cyclohexane, especially toluene, and further nonpolar solvents, and subsequently, more particularly with good mixing, with an aqueous alkali, preferably a strong alkali having a pH of at least 12, more preferably 13 to 14. The pH can be determined in a manner known per se to those skilled in the art, for example by means of pH paper. The alkali used is preferably an NaOH or KOH solution.

The concentration of the aqueous alkali can be selected such that the aqueous phase reaches a pH of 12 after the workup. pH values above 12 are preferable. The volume of the aqueous phase can be determined by the amount of NaCl formed during the workup, and generally depends on the free chloride content of the raw material.

The mixture thus obtained is suitably allowed to react while stirring for up to 30 minutes, preferably 15 seconds to 10 minutes, more preferably 20 seconds to minutes, even more preferably 25 seconds to 3 minutes, especially 30 seconds to 1 minute.

Preference is given to performing the workup at a temperature in the range from 5 to 100° C., more preferably from 10 to 60° C. and especially preferably in the range from 20 to 40°

C. Preference is given to working in a heatable/coolable stirred tank with a conically tapering bottom including bottom outlet and viewing window. Tank and stirrer are preferably made from a non-rusting material, for example stainless steel or enameled steel.

In general, two phases form after only a short rest time, which have a sharp separation from one another. After the formation of the two phases, the aqueous phase can be discharged from the organic phase via the bottom valve of the tank, and thus separated from the organic phase.

The aqueous phase generally contains the salt formed in the reaction in dissolved form; in the case of use of sodium hydroxide solution, the aqueous phase thus contains, for example, dissolved NaCl. The aqueous phase removed should suitably additionally have a pH of at least 12.

The organic phase can then be transferred into a further separating unit, for example into a distillation, or be conducted through a thin-film evaporator or through a short-path evaporator. The organic solvent, preferably toluene, is preferably removed therein, suitably by removal under reduced pressure.

The organic phase remains in the bottoms, and is suitably filtered and/or distilled to obtain a composition containing bis- and tris-amino-functional organosilanes. Thus, in accordance with the invention, it is possible to obtain a clear, generally colorless, yellow to deep orange, composition containing high-value bis- and tris-amino-functional organosilanes, which can be used advantageously for many applications in place of unbridged amino-functional organosilanes.

The organic phase obtainable by the process according to the invention can, however, also be subjected to a fine distillation in order thus to obtain the particular individual constituents of the organic phase obtained in accordance with the invention.

More particularly, the procedure in the process according to the invention may be as follows:

Preference is given to:

A) reacting a halogen-functional organosilane of the general formula (II)

in which X is Cl, Br or I, Z is a bivalent alkyl group from the group of —CH$_2$—, —(CH$_2$)$_2$—, —(CH$_2$)$_3$—, —(CH$_2$)$_4$— or —(CH$_2$)(CH)CH$_3$(CH$_2$)—, R' groups are the same or different and R' is a hydrogen (H) or a linear or branched alkyl group having 1 to 8 carbon atoms or an aryl group, R" groups are the same or different and R" is a linear or branched alkyl group having 1 to 8 carbon atoms or an aryl group, and n is 0, 1, 2 or 3, with excess ammonia or an organic amine of the general formula (III)

in which R groups are the same or different and R is hydrogen (H) or a linear or branched alkyl group having 1 to 4 carbon atoms, preferably H or n-butyl, and z is 0, 1 or 2, under pressure and with a temperature increase, preferably at 10 to 100 bar and 10 to 120° C., in the liquid phase, B) then removing excess ammonia or organic amine, for example by flashing off or distillation, to leave ammonium halide or organic amine hydrohalide dissolved fully in the liquid phase, C) transferring the liquid phase thus obtained to a crystallizer, the crystallizer being operated at a lower pressure level than the preceding reaction stage, and ammonium halide or organic amine hydrohalide and crude product are separated, D) distilling to obtain at least one amino-functional organosilane of the formula (Ia) from the crude product E) adding a nonpolar organic solvent and a strong aqueous alkali to the residue from the distillation, and mixing and allowing them to react, then separating the aqueous salt-containing phase from the organic phase, distilling the organic solvent out of the organic phase, and optionally filtering the organic phase remaining in the bottoms to obtain a composition containing bis- and tris-amino-functional organosilanes; cf. the formulae (Ib) and (Ic).

Thus, it is possible more particularly to obtain, in an advantageous manner, a composition containing bis- and tris-silylated amines of the formulae (Ib) and (Ic) with high addition of value from the residue from the distillation of the crude product (D), which is otherwise to be discarded.

Preference is given to performing the process according to the invention in the preparation of 1-aminomethyltrimethoxysilane, 1-aminomethyltriethoxysilane, 1-aminomethylmethyldimethoxysilane, 1-aminomethylmethyldiethoxysilane, 2-aminoethyltrimethoxysilane, 2-aminoethyltriethoxysilane, 3-aminopropyltrimethoxysilane (AMMO), 3-aminopropyltriethoxysilane (AMEO), 3-aminopropylmethyldimethoxysilane, 3-aminopropylmethyldiethoxysilane, N-methyl-3-aminopropyltrimethoxysilane, N-methyl-3-aminopropyltriethoxysilane, N-butyl-3-aminopropyltrimethoxysilane, 3-aminopropyldimethylmethoxysilane, 3-aminopropyldimethylethoxysilane, 3-aminopropyltrimethylsilane, 3-amino-2-methylpropyltrimethoxysilane, 3-amino-2-methylpropyltriethoxysilane, N-[2-aminoethyl]-3-aminopropyltrimethoxysilane (DAMO), N-[2-aminoethyl]-3-aminopropyltriethoxysilane, N-[2-aminoethyl]-3-aminopropylmethyldimethoxysilane, N-[2-aminoethyl]-3-aminopropylmethyldiethoxysilane, N,N-bis[2-aminoethyl]-3-aminopropyltrimethoxysilane, N,N-bis[2-aminoethyl]-3-aminopropyltriethoxysilane, N-[2-aminoethyl]-N'-[2-aminoethyl]-3-aminopropyltrimethoxysilane, N-[2-aminoethyl]-N'-[2-aminoethyl]-3-aminopropyltriethoxysilane, to name just a few examples, cf. formula (1a), and corresponding inventive compositions containing bis- and tris-amino-functional organosilanes, i.e. a composition which contains corresponding bis- and tris-silylated amines of the general formulae (Ib) and (Ic).

For the preferred performance of the process steps detailed above, especially of steps A to D, reference is additionally made to the contents of EP 1 295 889 A2, EP 1 209 162 A2, DE 101 40 563 A1 and EP 0 849 271 A2. These are fully incorporated in the disclosure of the present application.

In the above-described preferred embodiment of the process according to the invention, it is generally possible to react a halogen-functional organosilane of the general formula (II) with excess ammonia or an organic amine of the general formula (III) under pressure and with a temperature increase in the liquid phase. Subsequently, excess ammonia or organic amine can be flashed off or distilled off under pressure, in which case the ammonium halide or organic amine hydrohalide formed suitably remains fully dissolved in the liquid phase. The liquid phase thus obtained can then be transferred, for example, into a crystallizer, by initially charging the crystallizer with an organic liquid or organosilicon liquid or a mixture of said liquids, preferably toluene or hexane, heptane, octane, cyclohexane or a mixture thereof, and operating the crystallizer at a lower pressure level than the preceding reaction stage. In general, the residual amounts of ammonia or organic amine are distilled off, optionally additionally by temperature-controlled energy supply. The crystallizer can also be cooled. The salt which contains ammonium halide or organic amine hydrohalide and forms here in the crystallizer can then be removed from the crude product, for example by filtration, and the pure amino-functional organosilane can be obtained from the crude product in a manner known per se. To this end, an optionally fractional distillation is generally performed, which can be conducted under standard pressure or under reduced pressure. In the case that an organic amine is used, the salt residue from the crystallizer can advantageously be combined with the residue from distillation. Subsequently, the residues obtained can be worked up in accordance with the invention individually or together. For instance, to obtain a bis- and tris-amino-functional composition, in a simple and economically viable manner, an essentially nonpolar organic solvent and a strong aqueous alkali can be added to said residue, and the mixture can optionally be heated, mixed and preferably allowed to react in a controlled manner. Subsequently, the aqueous phase, which has advantageously virtually quantitatively taken up the salt, can be removed from the organic phase, and the solvent can be removed from the organic phase, preferably under reduced pressure. To obtain a composition containing bis- and tris-amino-functional organosilanes, cf. the general formulae (Ib) and (Ic), it is also possible to filter the organic phase remaining in the bottoms, for example by means of a filter or centrifuge. It is also possible for a residue containing ammonium halides or ammonium hydrohalides to remain, which can advantageously be recycled and especially combined with the residue from the crystallizer and/or the distillation, and worked up in accordance with the invention.

The present invention therefore also provides a composition containing bis- and tris-amino-functional organosilanes, which is obtainable by the process according to the invention.

More particularly, what is obtained in accordance with the invention is a composition with a content of 70 to 98 mol %, preferably 80 to 95 mol % and more preferably 88 to 91 mol % of bis-amino-functional organosilanes, 0 to 20 mol %, preferably 0.5 to 15 mol %, more preferably 4 to 8 mol % and even more preferably 4 to 6 mol % of tris-amino-functional organosilanes, 1 to 20 mol %, preferably 3 to 15 mol % and more preferably 4 to 6 mol % of so-called disiloxanes, and <20 ppm by weight of hydrolyzable halide, preferably <6 ppm by weight, down to the detection limit, based in each case on the overall composition. In addition, the inventive composition may contain small amounts of monosilylated amine, generally 0 to 10 mol %, for example 0.1, 0.5, 1, 1.5, 2 to 5 mol %, based on the composition.

Such a composition obtained from a residue in a simple and economically viable manner with high addition of value can then be used advantageously as an adhesion promoter, as a constituent in coating systems, as a constituent in paints and coating materials, as a drilling aid, as an agent or as an additive in the extraction and conveying of mineral oil, as evident, for example, from WO 05/124100, WO 05/124099, U.S. Pat. No. 4,498,538, U.S. Pat. No. 4,580,633 and US 2004/0177957 A1, as an agent or in an agent for reinforcement or integration of sand-rich soil layers in particular, as a constituent in epoxy resins and phenol resins, as a constituent in plastics, as a constituent in organically modified glasses, for the modification of glass fiber and mineral fiber surfaces, or the glass fiber reinforcement of plastics, as a constituent in sizes and for the treatment of fillers and pigments, and as an additive in adhesives and sealants—to name just a few advantageous application examples.

The present invention therefore likewise provides for the use of an inventive composition for the aforementioned applications.

The yield for the recovery of utilizable aminosilanes by the workup of said residues by the process according to the invention is advantageously about 98% or higher. The present invention is illustrated in detail by the example which follows, without restricting the subject matter.

EXAMPLES

Analytical Method by the Direct Potentiographic Titration of Hydrolyzable Chloride with Silver Nitrate Application Range
6-1 000 mg/kg
Chemicals
Water: distilled or deionized water
Acetic acid: for analysis, ≥99.8% (glacial acetic acid), shelf life 5 years
Ethanol: denatured, shelf life 10 years
Silver nitrate: 0.1 mol/l, calibration solution, for example ready to use from Merck, shelf life: 2 years, after opening 2 months
Silver nitrate: 0.01 mol/l or 0.005 mol/l, calibration solution, is prepared by diluting the solution from 6.4, shelf life 2 months
Sodium chloride: 0.01 mol/l, calibration solution: shelf life: 6 months Preparation of the calibration solution from an ampoule, e.g. Titrisol7 from Merck with c(NaCl)=0.1 mol/l
Instruments and Software
150 ml beakers, tall form
10 ml, 25 ml and 100 ml measuring cylinders
Automatic titrator: e.g. Metrohm 682 with silver rod electrode and Ag/AgCl reference electrode
Magnetic stirrer and teflon-sheathed stirrer bar
Procedure
The appropriate amount of sample is placed into a 150 ml beaker and admixed with 20 ml of ethanol and 80 ml of acetic acid. This is followed by potentiographic titration with silver nitrate solution. The same amount of reagent is used to determine a blank value.
Evaluation
The titroprocessor is generally programmed such that the proportion by mass of chloride in mg/kg is expressed directly after the titration.
For this and for the manual evaluation, the following formula applies:

$$\frac{(V_T - V_{BI}) \times c_{AgNO3} \times 35.5 \times 1000}{E} = \text{mg Cl}^-/\text{kg}$$

$V_T$=Consumption of $AgNO_3$ solution in ml
$V_{BI}$=Blank value determined of $AgNO_3$ solution in ml
$C_{AgNO3}$=Concentration of the $AgNO_3$ solution in mol/l
35.5=Molar mass of chloride in g/mol
1000=Conversion factor in g/kg
E=Starting weight in g
pH Determination:
pH values were determined by means of pH indicator strips (from Merck).

Example 1

EJ/V35/06

500 g of the brown residue with a chloride content of 7.2% by weight from the AMEO preparation process according to DE 101 40 563 A1 were admixed with 250 ml of toluene in a stirred apparatus at 50° C., and cooled to 25° C. Subsequently, an NaOH solution (62 g of NaOH, 200 g of $H_2O$) was added and the solution was stirred vigorously for 30 seconds. The phase separation was spontaneous. The aqueous phase was discharged. The NaCl was dissolved completely in the aqueous phase, and a pH of 14 was measured. The organic phase was freed of toluene at 80° C. under reduced pressure. The product was filtered.

This gave a clear and yellow-brown liquid with a hydrolyzable chloride content of <6 ppm by weight. GC analysis with internal standard showed 88% by weight of bis-AMEO, 8.0% by weight of tris-AMEO. A disiloxane content of 5.6 mol % was inferred from the $^{29}Si$ NMR spectrum. The yield was 95%.

The hydrolysis or condensation was examined by means of $^{29}Si$ NMR. Only a small increase in the M structures from 4.4 mol % to 5.6 mol % was found, i.e. barely any hydrolysis or condensation occurred during the aqueous workup.

Example 2

EJ/V32/06

500 g of the yellow residue with a chloride content of 7.5% by weight from the AMEO preparation process according to DE 101 40 563 A1 were admixed with 250 ml of toluene in a stirred apparatus at 50° C., and cooled to 25° C. Subsequently, an NaOH solution (62 g of NaOH, 150 g of $H_2O$) was added and the solution was stirred vigorously for 30 seconds. The phase separation was spontaneous. The aqueous phase was discharged. There were still small amounts of solid NaCl in the aqueous phase, and the pH of the aqueous phase was 14. The organic phase was freed of toluene at 80° C. under reduced pressure. The product was filtered.

This gave a clear and yellow liquid with a chloride content of 9.0 ppm by weight. GC analysis with internal standard showed 81.8% by weight of bis-AMEO, 5.7% by weight of tris-AMEO. A disiloxane content of 4 mol % was inferred from the $^{29}Si$ NMR spectrum. The yield was 98%.

Example 3

EJ/V33/06

500 g of the yellow residue with a chloride content of 7.1% by weight from the AMEO preparation process according to DE 101 40 563 A1 were admixed with 250 g of toluene in a stirred apparatus at 50° C., and cooled to 25° C. Subsequently, an NaOH solution (25.6 g of NaOH, 180 g of $H_2O$) was added and the solution was stirred vigorously for 30 seconds. The phase separation was spontaneous. The aqueous phase was discharged. There were still small amounts of solid NaCl in the aqueous phase, and the pH of the aqueous phase was 14. The organic phase was freed of toluene at 80° C. under reduced pressure. The product was filtered.

This gave a clear and yellow liquid with a chloride content of <6.0 ppm by weight. GC analysis with internal standard showed 88.1% by weight of bis-AMEO, 8.0% by weight of tris-AMEO. A disiloxane content of 5.3 mol % was inferred from the $^{29}Si$ NMR spectrum. The yield was 96%.

Example 4

EJ/V40/06

125 g of the yellow residue with a chloride content of 6.1% by weight from the AMEO preparation process according to DE 101 40 563 A1 were admixed with 31.25 g of toluene in a stirred apparatus at 50° C., and cooled to 25° C. Subsequently, an NaOH solution (15.5 g of NaOH, 50 g of $H_2O$) was added and the solution was stirred vigorously for 30 seconds. The phase separation was spontaneous. The aqueous phase was discharged. The NaCl formed was completely dissolved in the aqueous phase, and the pH of the aqueous phase was 14. The organic phase was freed of toluene at 80° C. under reduced pressure, and the product was filtered.

This gave a clear and yellow liquid with a hydrolyzable chloride content of 30 ppm by weight. GC analysis with internal standard showed 64.6% by weight of bis-AMEO, 6.6% by weight of tris-AMEO. A disiloxane content of 8.4 mol % was inferred from the $^{29}Si$ NMR spectrum. The yield was 89%.

Example 5

EJ/V76/06

546.8 g of a yellow residue comprising AMEO hydrochloride, bis-AMEO hydrochloride and tris-AMEO hydrochloride and with a chloride content of 5.2% by weight were admixed with 273.4 g of toluene in a stirred apparatus at 50° C., and cooled to 25° C. Subsequently, an NaOH solution (67.8 g of NaOH, 219.0 g of $H_2O$) was added and the solution was stirred vigorously for 30 seconds. The phase separation was spontaneous. The aqueous phase was discharged. The NaCl formed was completely dissolved in the aqueous phase, and the pH of the aqueous phase was 14. The organic phase was freed of toluene at 80° C. under reduced pressure. The product was filtered.

This gave a clear, yellow liquid with a hydrolyzable chloride content of <6 ppm by weight. GC analysis with internal standard showed 19.0% by weight of AMEO, 56.0% by weight of bis-AMEO, 12.0% by weight of tris-AMEO. A disiloxane content of 9.9 mol % was inferred from the $^{29}Si$ NMR spectrum. The yield was 92%.

Example 6

EJ/V80/06

286.0 g of a yellow residue comprising AMEO hydrochloride, bis-AMEO hydrochloride and tris-AMEO hydrochloride and with a chloride content of 6.2% by weight were admixed with 143 g of toluene in a stirred apparatus at 50° C., and cooled to 25° C. Subsequently, an NaOH solution (35.5 g of NaOH, 114.6 g of $H_2O$) was added and the solution was stirred vigorously for 30 seconds. The phase separation was spontaneous. The aqueous phase was discharged. The NaCl formed was completely dissolved in the aqueous phase, and the pH of the aqueous phase was 14. The organic phase was freed of toluene at 80° C. under reduced pressure. The product was filtered.

This gave a clear, yellow liquid with a hydrolyzable chloride content of 40 ppm by weight. GC analysis with internal standard showed 32.0% by weight of AMEO, 46.6% by weight of bis-AMEO, 12.4% by weight of tris-AMEO. A disiloxane content of 8.1 mol % was inferred from the $^{29}$Si NMR spectrum. The yield was 93%.

Example 7

EJ/V82/06

242.1 g of a yellow residue comprising AMEO hydrochloride, bis-AMEO hydrochloride and tris-AMEO hydrochloride and with a chloride content of 7.3% by weight were admixed with 143.2 g of toluene in a stirred apparatus at 50° C., and cooled to 25° C. Subsequently, an NaOH solution (35.5 g of NaOH, 114.6 g of H$_2$O) was added and the solution was stirred vigorously for 30 seconds. The phase separation was spontaneous. The aqueous phase was discharged. The NaCl formed was completely dissolved in the aqueous phase, and the pH of the aqueous phase was 14. The organic phase was freed of toluene at 80° C. under reduced pressure. The product was filtered.

This gave a clear, yellow liquid with a hydrolyzable chloride content of 9 ppm by weight. GC analysis with internal standard showed 19.4% by weight of AMEO, 52.6% by weight of bis-AMEO, 26.5% by weight of tris-AMEO. A disiloxane content of 6.3 mol % was inferred from the $^{29}$Si NMR spectrum. The yield was 95%.

Example 8

EJ/V91/06

125.0 g of a yellow residue comprising bis-AMMO hydrochloride and tris-AMMO hydrochloride and with a chloride content of 9.1% by weight were admixed with 125 g of toluene in a stirred apparatus at 50° C., and cooled to 25° C. Subsequently, an NaOH solution (15.5 g of NaOH, 50.0 g of H$_2$O) was added and the solution was stirred vigorously for 30 seconds. The phase separation was spontaneous. The aqueous phase was discharged. After an addition of 10 g of H$_2$O, the NaCl formed was completely dissolved in the aqueous phase, and the pH of the aqueous phase was 14. The organic phase was freed of toluene at 80° C. under reduced pressure. The product was filtered.

This gave a clear, yellow liquid with a hydrolyzable chloride content of <6 ppm by weight. GC analysis with internal standard showed 81.2% by weight of bis-AMMO, 7.0% by weight of tris-AMMO. The yield was 90%.

Example 9

EJ/V84/06

266.3 g of a yellow residue comprising DAMO hydrochloride, bis-DAMO hydrochloride and tris-DAMO hydrochloride and with a chloride content of 6.6% by weight were admixed with 155.6 g of cyclohexane in a stirred apparatus at 50° C., and cooled to 25° C. Subsequently, an NaOH solution (33.0 g of NaOH, 106.5 g of H$_2$O) was added and the solution was stirred vigorously for 30 seconds. The phase separation was spontaneous. The aqueous phase was discharged. The NaCl formed was completely dissolved in the aqueous phase, and the pH of the aqueous phase was 14. The organic phase was freed of cyclohexane at 80° C. under reduced pressure. The product was filtered.

This gave a clear, yellow liquid with a hydrolyzable chloride content of 720 ppm by weight. GC analysis with internal standard showed 23.2% by weight of DAMO, 56.2% by weight of bis-DAMO, 5.6% by weight of tris-DAMO. The yield was 85%.

The invention claimed is:

1. A process for working up a salt-containing residue from a preparation of an amino-functional organosilane of the formula (Ia):

$$R_2N[(CH_2)_2NH]_z(Z)Si(R'')_n(OR')_{3-n} \quad (Ia),$$

wherein

R groups are the same or different and R is hydrogen or a linear or branched alkyl group having 1 to 4 carbon atoms;

R' groups are the same or different and R' is hydrogen or a linear or branched alkyl group having 1 to 8 carbon atoms or an aryl group;

R" groups are the same or different and R" is a linear or branched alkyl group having 1 to 8 carbon atoms or an aryl group;

Z is a bivalent alkyl group selected from the group consisting of —CH$_2$—, —(CH$_2$)$_2$—, —(CH$_2$)$_3$—, —(CH$_2$)$_4$—, or —(CH$_2$)(CH)CH$_3$(CH$_2$)—;

n is 0, 1, 2, or 3; and z is 0, 1, or 2, wherein the salt-containing residue comprises at least one component selected from the group consisting of an ammonium halide and an organic amine hydrohalide, the process comprising:

(1) reacting at least one halogen-functional organosilane of the formula (II)

$$X—Z—Si(R'')_n(OR')_{3-n} \quad (II),$$

wherein

X is Cl, Br, or I;

Z is a bivalent alkyl group from the group of —CH$_2$—, —(CH$_2$)$_2$—, —(CH$_2$)$_3$—, —(CH$_2$)$_4$—, or —(CH$_2$)(CH)CH$_3$(CH$_2$)—;

R' groups are the same or different and R' is a hydrogen or a linear or branched alkyl group having 1 to 8 carbon atoms or an aryl group;

R" groups are the same or different and R" is a linear or branched alkyl group having 1 to 8 carbon atoms, or an aryl group; and n is 0, 1, 2, or 3, with an excess of ammonia or an organic amine of the formula (III)

$$RNH[(CH_2)_2NH]_zR \quad (III),$$

wherein

R groups are the same or different and R is hydrogen or a linear or branched alkyl group having 1 to 4 carbon atoms; and z is 0, 1 or 2, thereby obtaining a crude preparation of an amino-functional organosilane of the formula (Ia), and (2) subsequently separating the salt-containing residue by processing the crude preparation of the amino-functional organosilane and working up the obtained salt-containing residue by a process comprising:

(A) adding an nonpolar organic solvent and an aqueous alkali to the salt-containing residue to give a mixture;

(B) allowing the mixture to react and yield an aqueous phase and an organic phase;

(C) then separating the aqueous phase from the organic phase, comprising the nonpolar organic solvent; and (D) removing the nonpolar organic solvent from the organic phase, thereby obtaining a remaining organic phase comprising bis- and tris-amino-functional organosilanes, wherein the nonpolar organic solvent is added to the salt-containing residue after a distillation of the crude product, while stirring, wherein the aqueous alkali is added and said aqueous alkali is a strong aqueous alkali, wherein the aqueous alkali is a sodium hydroxide solution or potassium hydroxide solution, wherein the mixture is allowed to react with mixing up to 30 minutes so that to form the aqueous phase and the organic phase, and wherein the nonpolar organic solvent is added and is toluene.

2. The process according to claim 1, further comprising distilling the crude product, thereby obtaining the salt-containing residue prior to (2)(A).

3. The process according to claim 1, wherein the aqueous alkali is added and has a pH of from 12 to 14.

4. The process according to claim 1, wherein after the adding (A), the mixture is allowed to react while stirring for a period from 10 seconds to 30 minutes.

5. The process according to claim 1, wherein after the adding (A), the mixture is allowed to react at a temperature of from 5 to 100° C.

6. The process according to claim 1, wherein the removing (D) comprises distilling out the nonpolar organic solvent from the organic phase under reduced pressure.

7. The process according to claim 1, further comprising filtering the organic phase taken after the separating (C).

8. A process for preparing a composition comprising bis- and tris-amino-functional organosilanes, the process comprising:

(A) reacting a halogen-functional organosilane of the formula (II)

$$X-Z-Si(R'')_n(OR')_{3-n} \tag{II},$$ 

wherein

X is Cl, Br, or I;

Z is a bivalent alkyl group from the group of —CH$_2$—, —(CH$_2$)$_2$—, —(CH$_2$)$_3$—, —(CH$_2$)$_4$—, or —(CH$_2$)(CH)CH$_3$(CH$_2$)—;

R' groups are the same or different and R' is a hydrogen, a linear or branched alkyl group having 1 to 8 carbon atoms, or an aryl group;

R" groups are the same or different and R" is a linear or branched alkyl group having 1 to 8 carbon atoms or an aryl group; and n is 0, 1, 2, or 3, with excess of ammonia or an organic amine of the formula (III):

$$RNH[(CH_2)_2NH]_zR \tag{III},$$ 

wherein

R groups are the same or different and R is hydrogen or a linear or branched alkyl group having 1 to 4 carbon atoms; and z is 0, 1, or 2, under pressure and with a temperature increase in the liquid phase, (B) then removing excess of ammonia or the organic amine to leave an ammonium halide or an organic amine hydrohalide dissolved fully in the liquid phase;

(C) transferring the liquid phase obtained in (B) to a crystallizer, wherein the crystallizer is operated at a lower decreased pressure level than pressure in (B), and separating the ammonium halide or the organic amine hydrohalide from a crude product;

(D) distilling the crude product, thereby separating a salt-containing residue and at least one amino-functional organosilane of the formula (Ia) from the crude product $$R_2N[(CH_2)_2NH]_z(Z)Si(R'')_n(OR')_{3-n} \tag{Ia}$$ 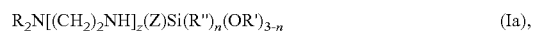

wherein

R groups are the same or different and R is hydrogen or a linear or branched alkyl group having 1 to 4 carbon atoms;

R' groups are the same or different and R' is hydrogen or a linear or branched alkyl group having 1 to 8 carbon atoms or an aryl group;

R" groups are the same or different and R" is a linear or branched alkyl group having 1 to 8 carbon atoms or an aryl group;

Z is a bivalent alkyl group selected from the group consisting of —CH$_2$—, —(CH$_2$)$_2$—, —(CH$_2$)$_3$—, —(CH$_2$)$_4$—, or —(CH$_2$)(CH)CH$_3$(CH$_2$)—;

n is 0, 1, 2, or 3; and z is 0, 1, or 2, and (E) adding a nonpolar organic solvent and a strong aqueous alkali to the salt-containing residue from the distilling (D), and mixing and allowing the alkali and the salt-containing residue to react and give an aqueous phase and an organic phase, then separating the aqueous phase, comprising a salt, from the organic phase and taking the organic phase, distilling the nonpolar organic solvent out of the organic phase to give a bottom composition, and, optionally, filtering the organic phase remaining in the bottom composition, wherein the nonpolar organic solvent is added to the salt-containing residue after a distillation of the crude product, while stirring, wherein the aqueous alkali is added and said aqueous alkali is a strong aqueous alkali, wherein the aqueous alkali is a sodium hydroxide solution or potassium hydroxide solution, and wherein the mixture is allowed to react with mixing up to 30 minutes so that to form the aqueous phase and the organic phase, thereby obtaining the composition comprising bis- and tris-amino-functional organosilanes.

9. The process according to claim 2, wherein the nonpolar organic solvent is toluene.

10. The process according to claim 1, wherein the nonpolar organic solvent is toluene.

11. The process according to claim 2, wherein the aqueous alkali is a sodium hydroxide solution or potassium hydroxide solution.

12. The process according to claim 1, wherein the aqueous alkali is a sodium hydroxide solution or potassium hydroxide solution.

13. The process according to claim 1, wherein the salt-containing residue is at least on residue selected from the group consisting of ammonium chloride, 3-aminopropyltriethoxysilane hydrochloride (AMEO hydrochloride), bis-AMEO hydrochloride, tris-AMEO hydrochloride, and a corresponding hydrolysis-related disiloxane.

14. The process according to claim 1, wherein the at least one halogen-functional organosilane is at least one selected form the group consisting of 3-chloropropyltrimethoxysilane, 3-chloropropyltriethoxysilane, 3-chloropropylmethyldimethoxysilane, 3-chloropropylmethyldiethoxysilane, 3-chloropropyldiethylmethoxysilane, and 3-chloropropylmethylpropylethoxysilane.

15. The process according to claim 1, wherein the aqueous alkali is added and has a pH of from 13 to 14.

16. The process according to claim 1, wherein after the adding (A), the mixture is allowed to react while stirring for a period from 30 seconds to 1 minute.

17. The process according to claim 1, wherein after the adding (A), the mixture is allowed to react at a temperature of from 20 to 40° C.

* * * * *